(12) United States Patent
Bates et al.

(10) Patent No.: US 9,229,071 B2
(45) Date of Patent: Jan. 5, 2016

(54) IDENTIFICATION OF MOLECULES BASED ON FREQUENCY RESPONSES USING ELECTROMAGNETIC WRITE-HEADS AND MAGNETO-RESISTIVE SENSORS

(75) Inventors: Allen Keith Bates, Tucson, AZ (US); Anna Wanda Topol, Jefferson Valley, NY (US); Daniel James Winarski, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 1061 days.

(21) Appl. No.: 13/151,258

(22) Filed: Jun. 1, 2011

(65) Prior Publication Data

US 2012/0310550 A1    Dec. 6, 2012

(51) Int. Cl.
  *G01N 27/00*   (2006.01)
  *G01R 33/00*   (2006.01)
  *G01R 33/09*   (2006.01)
  *G01R 33/12*   (2006.01)

(52) U.S. Cl.
  CPC .......... *G01R 33/093* (2013.01); *G01R 33/1269* (2013.01)

(58) Field of Classification Search
  USPC .......... 422/63–67; 436/526, 43–47, 149–151, 436/806
  See application file for complete search history.

(56) References Cited

U.S. PATENT DOCUMENTS

| | | | |
|---|---|---|---|
| 5,005,096 A | 4/1991 | Krounbi et al. | |
| 5,206,590 A | 4/1993 | Dieny et al. | |
| 5,452,164 A | 9/1995 | Cole et al. | |
| 5,465,185 A | 11/1995 | Heim et al. | |
| 5,689,384 A | 11/1997 | Albrecht et al. | |
| 5,764,567 A | 6/1998 | Parkin | |
| 6,282,051 B1 | 8/2001 | Albrecht et al. | |
| 6,320,719 B1 | 11/2001 | Albrecht et al. | |
| 6,592,820 B1 * | 7/2003 | Hardman et al. | 422/65 |
| 6,736,978 B1 | 5/2004 | Porter et al. | |
| 7,609,054 B2 | 10/2009 | Tondra et al. | |
| 8,283,916 B2 | 10/2012 | Llandro et al. | |
| 2007/0275396 A1 | 11/2007 | Zheng | |
| 2007/0279053 A1 * | 12/2007 | Taylor et al. | 324/252 |
| 2008/0207464 A1 | 8/2008 | Prins et al. | |
| 2008/0238411 A1 | 10/2008 | Kahlman et al. | |
| 2008/0284419 A1 | 11/2008 | Ikeda | |
| 2009/0104707 A1 | 4/2009 | Wang et al. | |
| 2009/0212768 A1 | 8/2009 | Llandro et al. | |
| 2009/0224755 A1 | 9/2009 | Kahlman et al. | |

(Continued)

OTHER PUBLICATIONS

Huang, T. S., et al. "Immobilization of antibodies and bacterial binding on nanodiamond and carbon nanotubes for biosensor applications." Diamond and related materials 13.4 (2004): 1098-1102.*

(Continued)

*Primary Examiner* — Lyle Alexander
*Assistant Examiner* — Robert Eom
(74) *Attorney, Agent, or Firm* — Zilka-Kotab, PC (57) ABSTRACT

The invention relates to the identification of molecules using electromagnetic write-heads and magneto-resistive sensors. In one embodiment, an electromagnetic write-head magnetically excites a molecule with an alternating magnetic field. A magneto-resistive sensor measures the resonant response of the magnetically excited molecule. A processor compares the resonant response to a table of known responses of different molecules to identify the chemical composition of the target molecule.

19 Claims, 7 Drawing Sheets

(56) References Cited

U.S. PATENT DOCUMENTS

| | | |
|---|---|---|
| 2010/0109657 A1 | 5/2010 | Voegeli |
| 2011/0076670 A1 | 3/2011 | Boday et al. |
| 2011/0077869 A1 | 3/2011 | Boday et al. |

OTHER PUBLICATIONS

Osterberg, Frederik W., et al. "Bead capture on magnetic sensors in a microfluidic system." Sensors Journal, IEEE 9.6 (2009): 682-688.*

K. Bourzac, "A Way to Spot Cancer Early," MIT Technology Review, Dec. 19, 2008, http://www.technologyreview.com/biomedicine/21908/.

S. J. Osterfeld et al., "Multiplex protein assays based on real-time magnetic nanotag sensing," PNAS, vol. 105, Dec. 30, 2008, pp. 20637-20640.

J. Liandro et al., "Magnetic biosensor technologies for medical applications: a review," Med. and Biol. Eng. and Computing, Springer Berlin, online Jun. 23, 2010.

Boday et al., U.S. Appl. No. 12/888,388, filed on Sep. 22, 2010.

Boday et al., U.S. Appl. No. 12/888,408, filed on Sep. 22, 2010.

Ostrovsky, G., "Giant Magnetoresistance Now for Cancer Detection," Article retrieved from Medgadget from: http://www.medgadget.com/2008/12/giant_magnetoresistance_now_for_cancer_detection.html, Dec. 22, 2008, pp. 1-2.

Ostrovsky, G., "Giant Magnetoresistance Now for Cancer Detection," Article retrieved from Medgadget from: http://www.medgadget.com/2008/12/giant_magnetoresistance_now_for_cancer_de tection.html, Apr. 27, 2015, pp. 1-2.

* cited by examiner

IDENTIFICATION OF MOLECULES BASED ON FREQUENCY RESPONSES USING ELECTROMAGNETIC WRITE-HEADS AND MAGNETO-RESISTIVE SENSORS

The invention relates to analytical devices and processes, and more particularly, to devices and processes that incorporate electromagnetic write-heads and magneto-resistive read-sensors to identify the chemical composition of molecules based on the frequency responses of magnetically excited molecules.

BACKGROUND

Microchip sensors are incorporated into bio-assay devices and systems to detect the presence of viruses, cancer proteins, and other biological substances of interest. The microchip sensors may be in the form of silicon chip arrays and contain thousands of sensors, each coated with a different antibody that would latch on a particular virus or protein, and thus indicating the presence of target viruses or proteins and their concentration in a biological sample.

It is desirable to exploit the use of magnetic signaling technology to automate the identification of molecules, such as viruses and cancer proteins, and to further apply this technology to the detection of any biological matter.

BRIEF SUMMARY OF THE DISCLOSURE

Exemplary embodiments of the invention relate to analytical devices and processes. More particularly, the embodiments provide an apparatus, method, and computer program product that use electromagnetic write-heads and magneto-resistive read-sensors to identify the chemical composition of molecules based on the frequency responses of magnetically excited molecules.

In an exemplary embodiment of the invention, an apparatus for identifying a molecule is disclosed. The apparatus comprises an electromagnetic write-head to magnetically excite the molecule with an alternating magnetic field, a magneto-resistive sensor for measuring the resonant response of the magnetically excited molecule, and a processor for comparing the resonant response to a table of known responses to identify the chemical composition of the molecule.

In another exemplary embodiment, a method for identifying a molecule is disclosed. The method comprises magnetically exciting the molecule with an alternating magnetic field generated by an electromagnetic write-head, measuring a resonant response of the molecule with a magneto-resistive sensor, and comparing the resonant response to a table of known responses to identify the chemical composition of the molecule.

In a further embodiment, a computer program product for identifying a molecule is disclosed. The computer program product comprises a computer readable storage medium having computer readable program code embodied therewith. The computer readable program code is configured to magnetically excite the molecule with an alternating magnetic field generated by an an electromagnetic write-head, measure a resonant response of the molecule with a magneto-resistive sensor, and compare the resonant response to a table of known responses to identify the chemical composition of the molecule.

For a fuller understanding of the invention, reference is made to the following detailed description taken in conjunction with the accompanying drawings.

DETAILED DESCRIPTION

Embodiments of the invention relate to methods and systems for identifying molecules in biosamples using electromagnetic thin-film write-heads and magneto-resistance read-sensors. The invention is described in exemplary embodiments with reference to the Figures, in which like numbers represent the same or similar elements. It will be appreciated by those skilled in the art that variations may be accomplished in view of these teachings without deviating from the spirit or scope of the invention.

Figure 1:
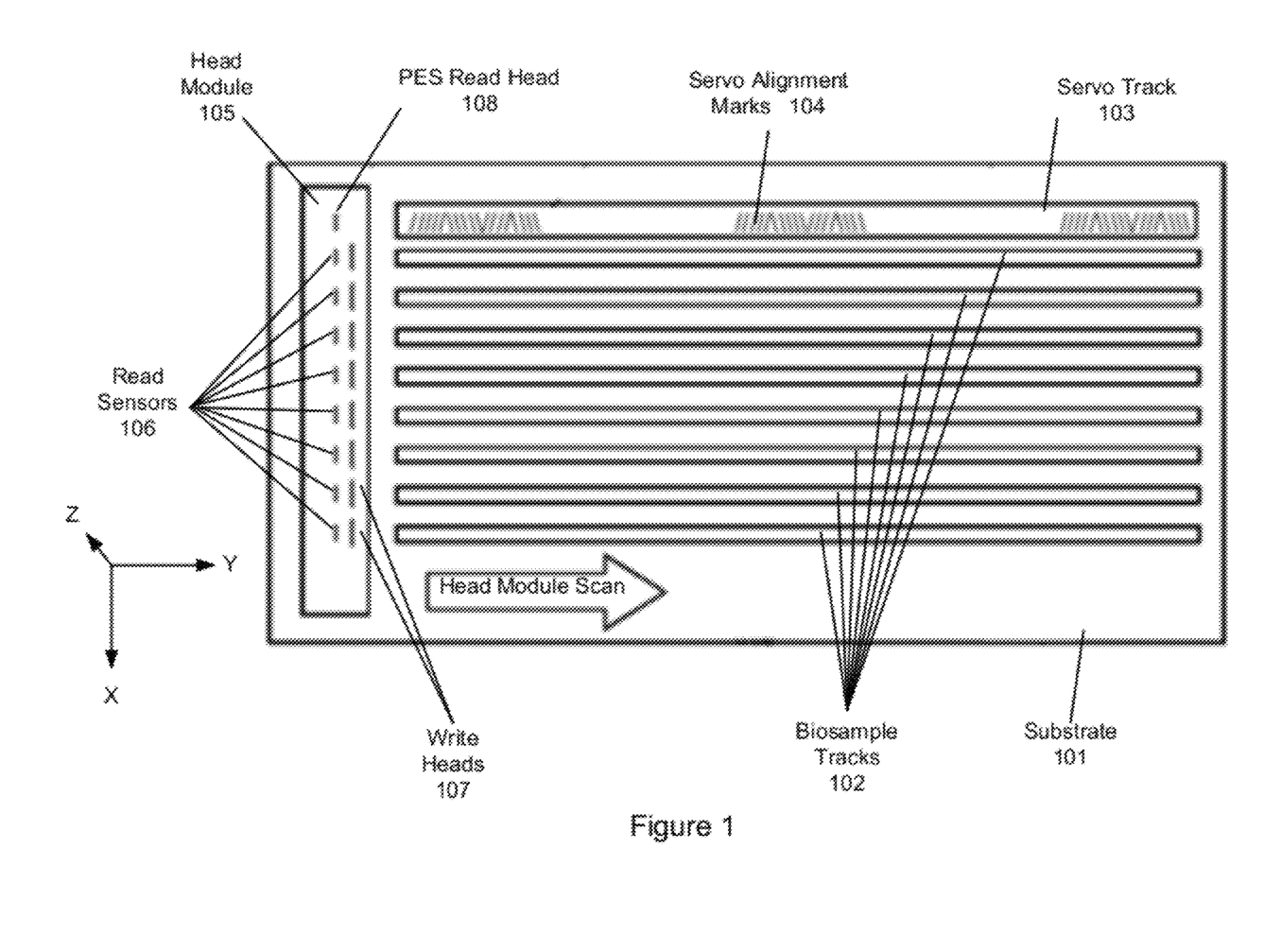
FIG. 1 illustrates a top view of an exemplary substrate that includes biosample tracks for carrying biosample molecules that may be scanned and identified by the embodiments of the invention.

Referring to FIG. 1, there is illustrated a top view of an example substrate 101, which may comprise a Peltier™ hard-substrate, a glass substrate, a polyethylene terephthalate (PET, which is commonly known by the trade name of Mylar™) flexible-substrate, or other materials having similar properties. In an exemplary embodiment of the invention, head-module 105 scans across stationary substrate 101 from left-to-right, along the +Y-axis, individually sampling one or simultaneously sampling a plurality of biosample tracks 102. Alternatively, substrate 101 may be swept across stationary head-module 105 from right-to-left, along the −Y-axis. If substrate 101 is of a flexible polyethylene terephthalate material, then in one embodiment, this right-to-left motion may be performed as data read-write operations in a magnetic tape drive. As an alternate embodiment of the invention, head-module 105 comprises a helical-scan rotary head-module, and the Y-axis of the biosample tracks 102 is at an angle to the substrate.

FIG. 1 shows electromagnetic write-heads 107 and magneto-resistive read-sensors 106 arranged in pairs in head-module 105. In one embodiment, write-heads 107 and read-sensors 106 are on the same head-module 105. In an alternate embodiment, write-heads 107 and read-sensors 106 may be independently adjustable. In yet another embodiment, a write-head 107 and a read-sensor 106 in a pair may be orthogonal to one another so that the magnetic excitation signal of write-head 107 is less dominant to read-sensor 106. The electromagnetic write-heads 107 first write to biosample tracks 102, and then the adjacent magneto-resistive read-sensors 107 immediately read from biosample tracks 102, which is referred to as a read-after-write operation. The magnetic excitation of a molecule by a write-head 107 may be done with a "spike" or impulse signal. In an alternate embodiment, the write head 107 magnetically excites the molecule with a swept sine or random noise magnetic-excitation and the read head simultaneously reads the resonant response of the molecule.

In an exemplary embodiment of the invention, substrate 101 comprises eight biosample tracks 102 corresponding to eight bits in a byte, and hence to eight electromagnetic write-head 107 and magnetoresistive read-sensor 106 pairs in a typical head-module 105 used in magnetic tape drive products. However, as alternatives, any number of biosample tracks 102 may be used. The number of electromagnetic write-head 107 and magneto-resistive read-sensor 106 pairs in head-module 105 may be any number ranging from a minimum of one to the number of electromagnetic write-head and magneto-resistive read-sensor pairs in the head-modules of the tape drives. For example, there are sixteen such electromagnetic write-head and magneto-resistive read-sensor pairs in a head module of an IBM 3480™ tape drive. Typically, the number of biosample tracks 102 is an integral multiple of the number of write-head 107 and read-sensor 106 pairs. In an alternate embodiment, a single device may perform the functions of both the write-head 107 and read-sensor 106.

Write-heads 107 may comprise miniature electromagnets, with a coil sandwiched between to poles, such as taught without limitation by U.S. Pat. No. 5,452,164, entitled "Thin Film Magnetic Write-head," which is hereby incorporated by reference in its entirety. Write-heads 107 may comprise other structures with similar functionality.

Read-sensors 106 may be anisotropic magneto-resistive (AMR), giant magneto-resistive (GMR), or tunnel magneto-resistive (TMR) read-sensors, or other devices having similar functionality. AMR read-sensors are taught without limitation by U.S. Pat. No. 5,005,096, entitled "Magnetoresistive Read Transducer Having Hard Magnetic Shunt Bias," which is hereby incorporated by reference in its entirety. AMR read-sensors may comprise other structures having similar functionality. GMR read-sensors, which are also known as spin-valve read-sensors, are taught without limitation by U.S. Pat. No. 5,206,590, entitled "Magnetoresistive Sensor Based On The Spin Valve Effect," which is hereby incorporated by reference in its entirety. GMR read-sensors may comprise other structures having similar functionality.

The GMR read-sensors typically have an internal antiparallel pinned layer for increased sensitivity, as taught without limitation by U.S. Pat. No. 5,465,185, entitled "Magnetoresistive Spin Valve Sensor With Improved Pinned Ferromagnetic Layer And Magnetic Recording System Using The Sensor," which is hereby incorporated by reference in its entirety. A recent form of read-sensor, TMR, uses a tunnel barrier layer to augment the GMR internal structure and to provide increased sensitivity, as taught without limitation by U.S. Pat. No. 5,764,567, entitled "Magnetic Tunnel Junction Device With Nonferromagnetic Interface Layer For Improved Magnetic Field Response," which is hereby incorporated by reference in its entirety. TMR read-sensors may comprise other structures having similar functionality.

In the exemplary embodiment illustrated in FIG. 1, write-head 107 is longer along the X-axis direction than read-sensor 106. The active sensing portion of read-sensor 106 is smaller than write-head 107, along the X-axis, as write-head 107 is used to magnetically excite molecule 302 as described with reference to FIG. 3, for identifying the molecule 302 by read-sensor 106. If read-sensor 106 were too large in the X-axis direction, it could potentially encounter non-magnetically excited molecules 302 and thus register an undesired false identification of molecule 302, as described with reference to FIG. 3.

Head-module 105 may be maintained in linear alignment with biosample tracks 102 along the X-axis by position-error-servo (PES) read-head 108, which reads magnetically encoded servo-alignment marks 104 from servo track 103 on substrate 101. PES read-head 108 may be, for example, an AMR, GMR, or TMR read-sensor. Magnetically encoded servo alignment marks 104 are encoded by the manufacturer of substrate 101 on either a piece of magnetic tape adhered to substrate 101 or encoded on a magnetic recording layer directly deposited on substrate 101.

In the example illustrated in FIG. 1, particular servo-alignment marks 104 shown in servo track 103 are Timing Based Servo (TBS) servo-alignment marks such as those used in IBM's Linear Tape Open (LTO) tape drive products, e.g., IBM tape drive models TS1120™ and TS1210™. TBS servo-alignment marks are taught without limitation by U.S. Pat. No. 6,320,719, entitled "Timing Based Servo System for Magnetic Tape Systems," which is hereby incorporated by reference in its entirety. Servo-alignment marks 104 may comprise other structures with similar functionality. The writing of TBS servo-alignment marks 104 in servo track 103, as shown in FIG. 1, is taught without limitation by U.S. Pat. No. 6,282,051, entitled "Timing Based Servo System for Magnetic Tape Systems," which is hereby incorporated by reference in its entirety. TBS servo-alignment marks 104 may comprise other structures with similar functionality.

Figure 2:
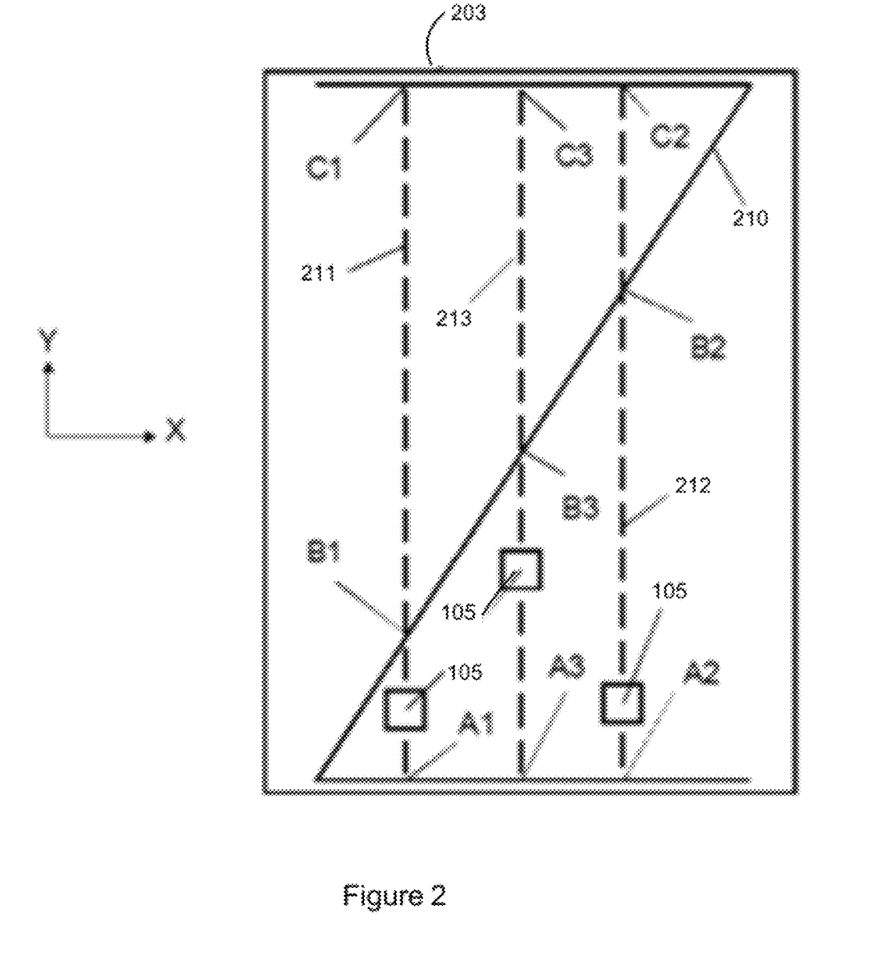
FIG. 2 is a block diagram of an exemplary Z-pattern servo-alignment mark for aligning an electromagnetic read-write head with a biosample track, in accordance with an embodiment of the invention.

FIG. 2 illustrates an exemplary embodiment of servo-alignment marks 104 in the form of magnetically-encoded Z-pattern 210 that comprises servo-alignment marks in servo track 203. Relative to the Y-axis, the distance between the top and bottom legs of Z-pattern 210 is constant and equal to the sum of line segments AB and BC, which is equal to the sum of line segments A1B1 and B1C1 in path 211. This distance is also equal to the sum of line segments A2B2 and B2C2 in path 212, and the sum of line segments A3B3 and B3C3 in path 213. Thus, the velocity of head module 105 along the Y-axis relative to substrate 101 may be calculated by dividing the sum of line segments (AB+BC) by the time to transit Z-pattern 210 by head module 105. This velocity calculation is not affected by the position of PES read-head 108 along the X-axis, because the top and bottom of Z-pattern 210 are both parallel to the X-axis.

The position-error-servo (PES) signal corresponding to the position of PES read-head 108, and hence write-heads 107 and read-sensors 106, along the X-axis may be determined by subtracting the distance AB from the distance BC each time a Z-pattern 210 is encountered by PES read-head 108. As can be seen in FIG. 2, the PES signal from PES read-head 108 following path 212 is less than zero because the distance difference (B2C2−A2B2) is less than zero. Similarly, the PES signal from PES read-head 108 following path 211 is greater than zero because the difference (B1C1−A1B1) is greater than zero. Additionally, the value of (BC−AB) varies linearly as PES read-head 108 moves from left to right along the X-axis. Thus the PES signal, as calculated by the difference in distance (BC−AB), provides an X-axis PES signal for head-module 105 and its pairs of electromagnetic write-heads 107 and magneto-resistive read-sensors 106. This PES signal is incorporated into servo control circuit 500 shown in FIG. 5.

In an exemplary embodiment of the invention, the value of the line segment difference (BC−AB) is evaluated based on the time it takes for the PES read head 108 to cross segments AB and BC when the head-module 105 is moving at a constant velocity during its Y-axis seek operation. This is the case where the transit time for the PES read head 108 to cross each Z-pattern 210 is constant. In the exemplary embodiments of the invention shown in FIGS. 1 and 2, TBS servo-alignment marks 104 and Z-pattern 210 could be non-magnetic stripes, either lithographed, silk-screened, or ink-jet printed, and read with an optical laser.

In FIG. 2, path 213 is the desired path for PES read-head 108 as electromagnetic write-heads 107 and magneto-resistive read-sensors 106 are aligned with biosample tracks 102. With path 213, the distance difference (B3C3−A3B3) is equal to zero, i.e., line segment B3C3 is equal to line segment A3B3. For path 211, the distance difference (B1C1−A1B1) is greater than zero, which means that head-module 105 must be moved in the +X direction by X-axis actuator 529 of FIG. 5 so that electromagnetic write-heads 107 and magneto-resistive read-sensors 106 are aligned with biosample tracks 102. The operation of the X-axis actuator 529 is described below with reference to FIG. 5. Similarly, for path 212, the distance difference (B2C2−A2B2) is less than zero, which means that head-module 105 must be moved in the −X direction by X-axis actuator 529 so that electromagnetic write-heads 107 and magneto-resistive read-sensors 106 are aligned with biosample tracks 102.

Figure 3:
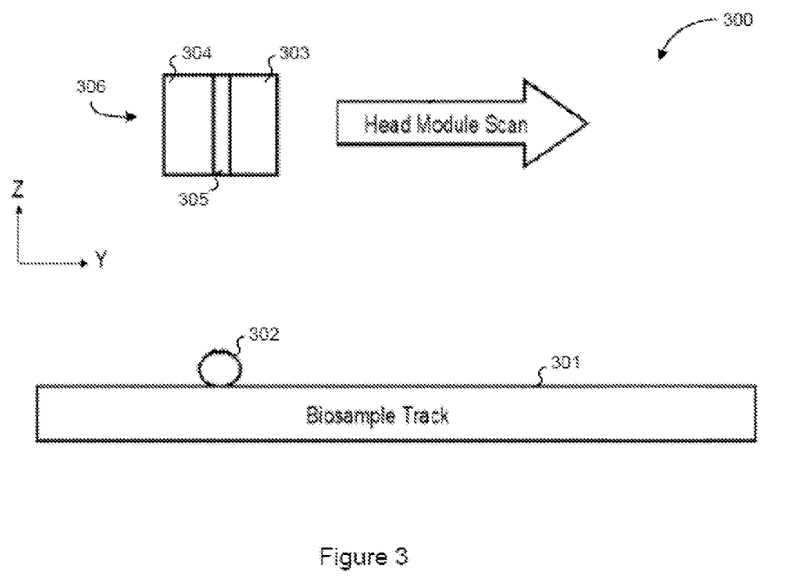
FIG. 3 is a block diagram of a side view of an exemplary biosample track relative to an electromagnetic read-write head for analyzing and identifying molecules in a biosample, in accordance with an embodiment of the invention.

FIG. 3 illustrates a side view of an exemplary biosample track relative to an electromagnetic read-write head for analyzing a biosample. A biosample track 301 may be deposited on a substrate such as a Peltier™ substrate or a magnetic tape media as described in FIGS. 1 and 2. A biosample 302 may be positioned on the biosample track 301 to be analyzed by an electromagnetic read-write head 306 in accordance with an embodiment of the invention. Magnetic shield 305 separates write-head 303 and read-sensor 304 so that there is no meaningful cross-talk between write-head 303 and read-sensor 304 while the electromagnetic read-write head module 306 scans along the biosample track 301. The scan may be performed by moving head-module read-write head module 306 linearly in the +Y direction relative to biosample track 301, which could equally be done by moving the substrate carrying the biosample track 301 linearly in the −Y direction relative to read-write head-module 306. In an alternate embodiment, write-head 303 and read-sensor 304 may switch positions.

Figure 4A:
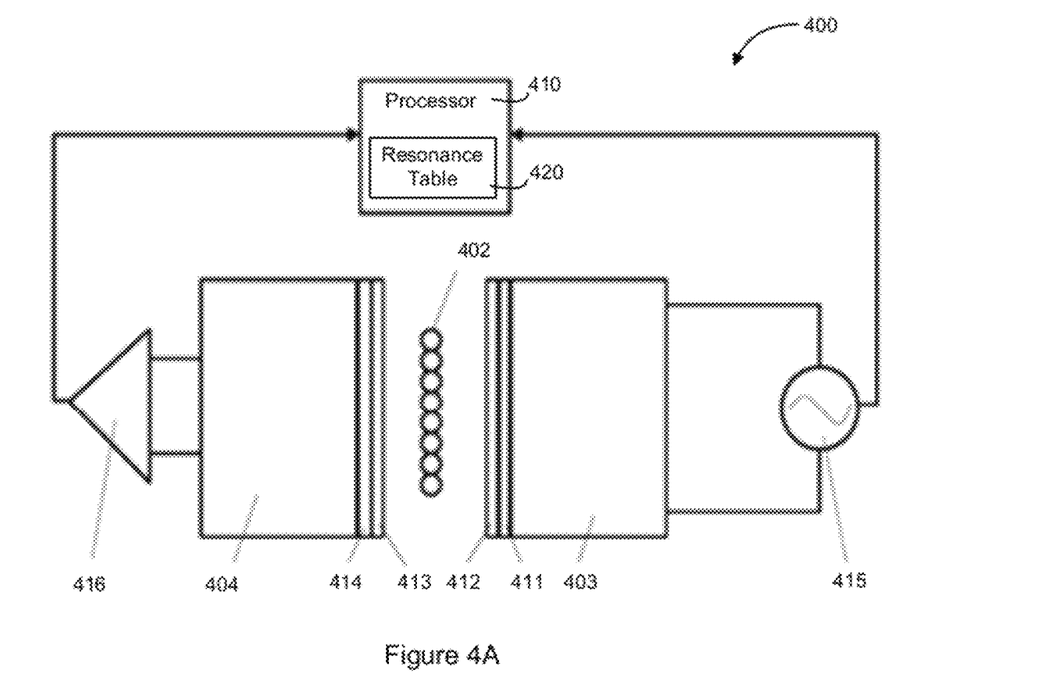
FIG. 4A illustrates a block diagram of a system for identifying a molecule using an electromagnetic read-write head, in accordance with an embodiment of the invention.

FIG. 4A illustrates a block diagram of a molecule analysis system 400 for magnetically exciting molecules 402 in a biosample 302 and identifying the molecules 402 based on the frequency responses of the magnetically excited molecules, in accordance with an embodiment of the invention. The molecule analysis system 400 comprises an electromagnetic thin-film write-head 403 for magnetically exciting the molecules 402 in the biosample 302 while the electromagnetic thin-film write-head 403 scans biosample track 301.

In one embodiment, the electromagnetic thin-film write-head 403 may magnetically excite the molecules 402 using a swept-sine signal. The swept-sine signal is a sine wave with a frequency that increases over time and may be generated by a signal generator 415. The electromagnetic thin-film write-head 403 may magnetically excite the biosample molecules 402 using a range of frequencies in order to magnetically excite the molecules 402 with an alternating magnetic field. In another embodiment, the electromagnetic thin-film write-head 403 may magnetically excite the molecules 402 using an impulse signal having a generally narrow square-wave spike that is applied once during the measurement of the resonant response. Alternatively, the electromagnetic thin-film write-head 403 may magnetically excite the biosample molecules 402 with an alternating magnetic field that is generated by a random-noise signal. The random noise signal may be produced by sending a reverse polarity voltage across a diode.

In another embodiment, the analytical system 400 may further expose the molecules 402 to a direct current (DC) magnetic field while the molecules 402 are being magnetically excited to facilitate the measurement of the resonant responses from the magnetically excited molecules 402. A permanent magnet or an electromagnet may be used to provide such a DC magnetic field. The DC magnetic field aligns the magnetically excited molecules 402 for improved signal-to-noise ratio during the alternating magnetic field excitation.

The electromagnetic thin-film write-head 403 may be coated in one or more protective layers such as a diamond carbon layer 411 to act as an electrical insulator between the biosample molecules 402 and the electromagnetic thin-film write-head 403. An outer layer 412, which may be gold or platinum, covers the diamond carbon layer 411 and thin-film write-head 403 to protect the thin-film write-head 403 from corrosion caused by the salinity in the biosample 302.

The molecule analysis system 400 further comprises an electromagnetic read-sensor 404 for sensing the frequency responses of the magnetically excited molecules 402. Molecules 402 are comprised of atoms which are bonded together by ionic or covalent bonds. A mass-spring mechanical system, such as a car and its springs, will resonate at a natural frequency which is a function of the square root of the spring rate (in Newtons per meter) divided by the mass (kilograms), and a multiple spring-multiple mass system will have multiple resonances. By analogy, bonds between atoms in molecules provide a spring action and the atoms themselves possess mass, and thus molecules can have multiple resonances which are a function of the chemical makeup of the molecule. It is these resonances that are excited by write-head 403.

Figure 4B:
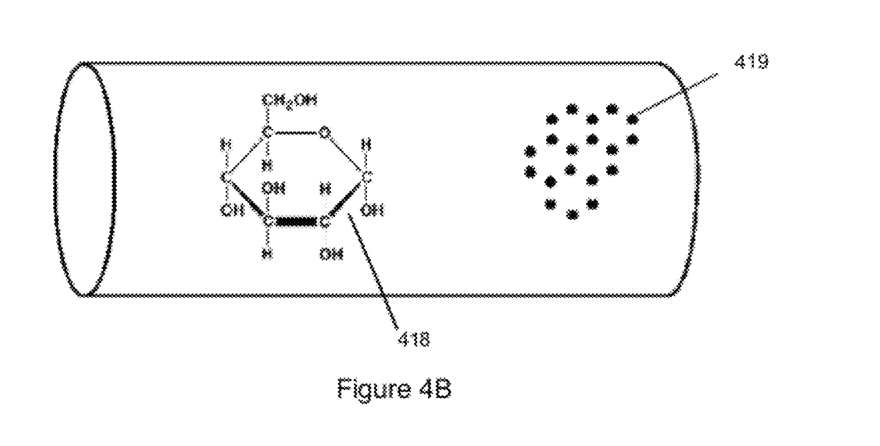
FIG. 4B illustrates an example of a glucose molecule being encapsulated in a carbon nanotube, in accordance with an embodiment of the invention.

A target molecule 402 may be held in position during its magnetization by encapsulating it in a carbon nanotube. As an example, FIG. 4B illustrates an example of a glucose molecule 418 being encapsulated in a carbon nanotube 419. In an alternate example, a target molecule 402 may be held in place by an antibody, as taught in the commonly-assigned patent application entitled "Detection Of Analytes Via Nanoparticle-Labeled Substances With Electromagnetic Read-Write Heads", Ser. No. 12/888,388, herein incorporated by reference in its entirety. In another alternate embodiment, the target molecule 402 is held in position by surface aligned molecules (SAMs). In yet another alternate embodiment, target molecule 402 is held in a liquid suspension, such as a saline suspension. The resonant response of the antibody, SAMs, and liquid suspension are first gathered without the target molecule 402 so that the resonant response of the target molecule 402 can be isolated from the surrounding environment.

The electromagnetic read-sensor 404 may be a giant magneto-resistance (GMR) sensor, a tunnel magneto-resistance (TMR) sensor, or an anisotropic magneto-resistance (AMR) sensor. Similarly to the thin-film write-head 403, the electromagnetic read-sensor 404 may be coated in one or more protective layers such as a diamond carbon layer 414 to act as an electrical insulator between the biosample molecules 402 and the electromagnetic read-sensor 404. An outer layer 413, which may be gold or platinum, covers the diamond carbon layer 414 and electromagnetic read-sensor 404 to protect the electromagnetic read-sensor 404 from corrosion caused by the salinity in the biosample 303.

The frequency responses of the magnetically excited biosample molecules 402 that are detected by the electromagnetic read-sensor 404 are generally small, for example, on the order of 0.1 to 10 microvolts. The molecule analysis system 400 may comprise an amplifier 416 for amplifying the detected response, which is then further processed by processor 410 to identify the molecules 402. For example, a solid-state voltage amplifier having a gain ranging from 10× to 1000× may be used.

In one embodiment, the processor 410 may compare the amplified frequency responses, or a range of responses, of the magnetically excited biosample molecules 402 to a table of known frequency responses of a group of molecules. For example, the sucrose molecule, C12H22O11, will have different resonances than that of polytetrafluoroethylene, C2F4. By identifying the resonances as a function of their frequency and amplitude, the molecule analysis system 400 can identify whether a molecule is sucrose or polytetrafluoroethylene.

In another embodiment, the processor 410 may calculate Bode plots of the frequency response of a molecule divided by the excitation signal to detect tell-tale resonances. The Bode plots may be calculated by dividing the Fourier transform $F(\omega)$ of the amplified frequency response (i.e., the output of the amplifier 416) by the Fourier transform of the signal from the signal generator 415, in order to normalize the resonant response to the magnetic-excitation. Alternatively, processor 410 could use power spectrum or Fourier transforms of the output of the electromagnetic read-sensor 404 to detect tell-tale resonances. The power spectrum is the square of the magnitude of the Fourier transform output and is calculated by taking the product of the Fourier transform times its complex conjugate. The power spectrum is useful because there is no phase, only amplitude, and thus resonances are readily identified.

The Bode plot is the most useful for detecting the tell-tale resonances as the output of the electromagnetic read-sensor 404 may be normalized to the excitation signal to facilitate the identification of tell-tale resonances. Processor 410 may access an internal table 420 of known resonant responses for different biosample molecules 402 and match the measured resonant response with the internal table 420 to identify the biosample molecules 402. The internal table 420 is stored in a nonvolatile portion of processor 410 and may include a list of known molecules and their resonant frequencies, as well as normalized amplitudes of those resonant frequencies.

As an example, resonances R1 and R2 may have generally the same amplitudes but resonance R3 has generally twice the amplitudes of resonances R1 and R2. The table may include harmonics of these resonant frequencies, if they exist. For example, resonant frequency R1 has a first harmonic at frequency 2*R1 and a second harmonic at frequency 3*R1, but no additional harmonics of frequency R1 are present. The molecule analysis system 400 may look up the resonant frequencies, normalized amplitudes, and harmonic frequencies in identifying the chemical composition of a molecule.

Figure 6:
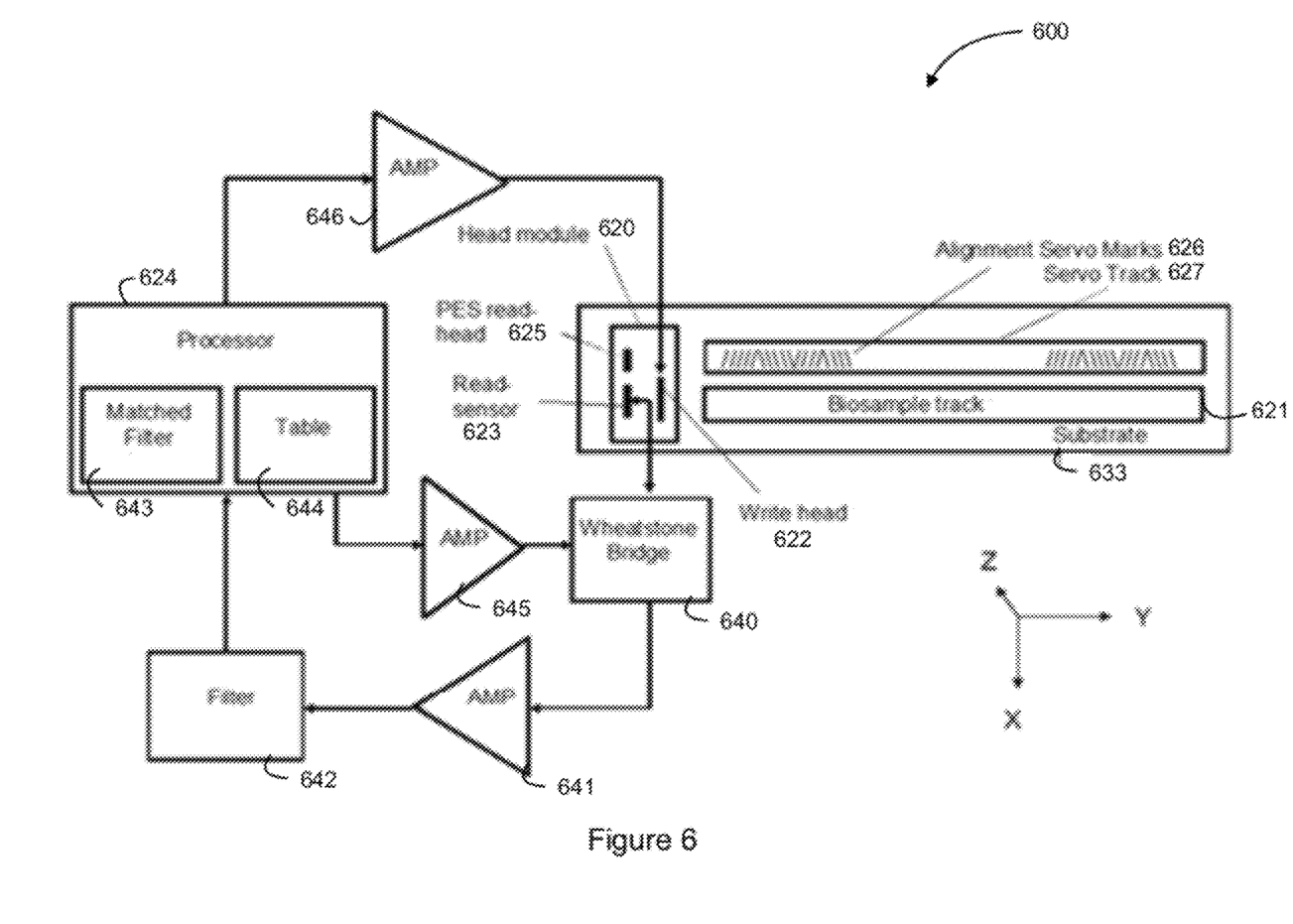
FIG. 6 is a block diagram of an exemplary write and read circuit for use with an analytical device, in accordance with an embodiment of the invention.

In one embodiment, the molecule analysis system 400 may filter out DC signals from the measured resonant response of the magnetically excited molecules 402 to improve the signal-to-noise ratio (SNR) of the response. The removal of the unwanted DC signals may be accomplished by balancing a resistive Wheatstone bridge in which one leg of the Wheatstone bridge contains the magneto-resistive sensor. An example of the use of a Wheatstone bridge in a molecule resonance sensing circuit is illustrated in FIG. 6.

In another embodiment, the molecule analysis system 400 may further filter out AC noise signals from the measured resonant response of the magnetically excited molecules 402 to improve the signal-to-noise ratio (SNR) of the response, using a filter. AC noises, such as those introduced by lighting and electric power equipment in a laboratory, may be removed using a band pass filter, band block filter, high-pass filter, Hamming filter, or Butterworth filter, which are known to one skilled in the art.

Figure 5:
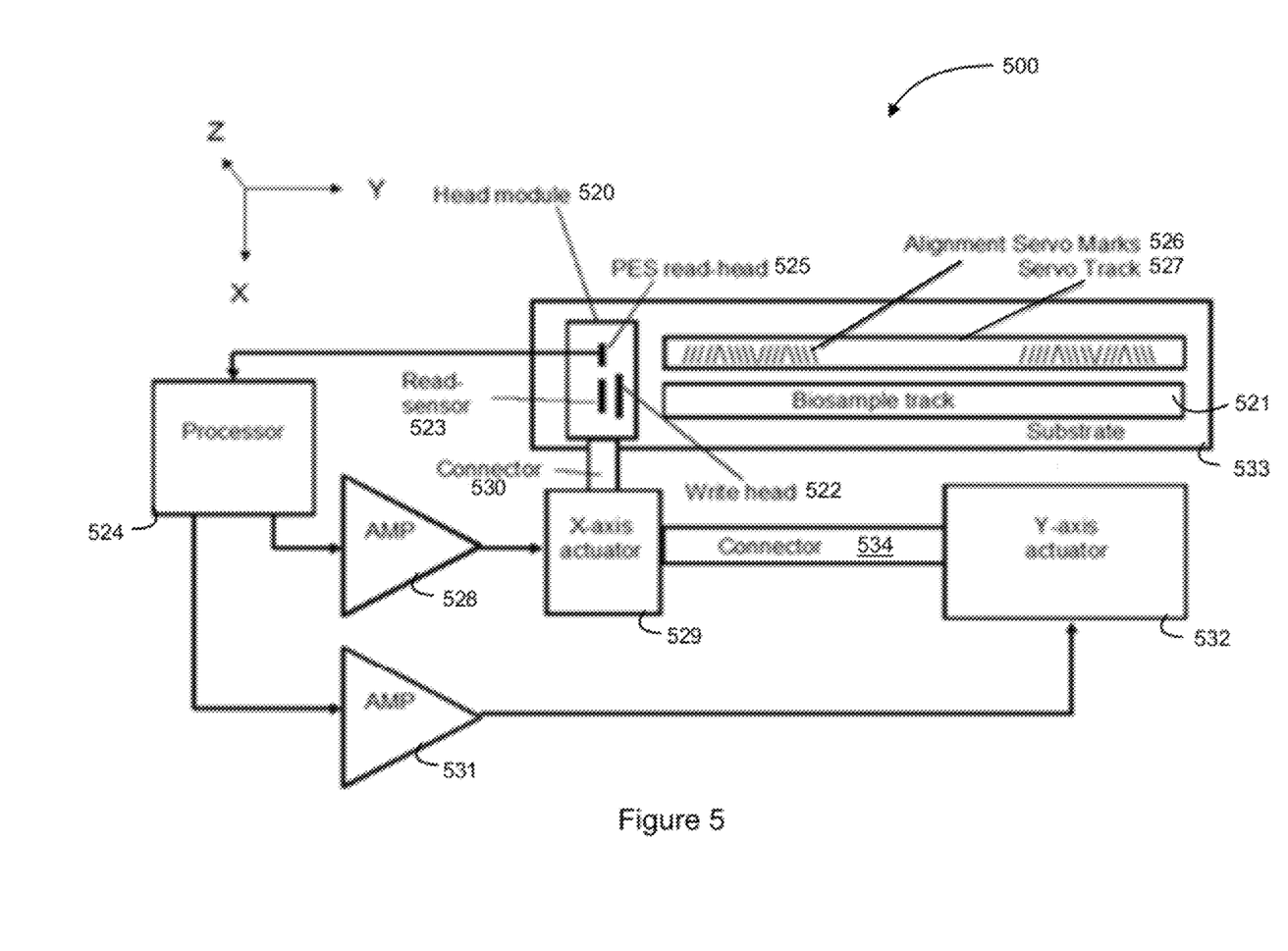
FIG. 5 is a block diagram of an exemplary circuit for controlling the X-axis and Y-axis motion of the read-write head-module of an analytical device, in accordance with an embodiment of the invention.

FIG. 5 shows an exemplary embodiment of a servo control system 500 for controlling the X-axis and Y-axis motion of head-module 520. As an example, FIG. 5 shows one biosample track 521, and one pair of write-head 522 and read-sensor 523. Processor 524 receives position-error-servo (PES) signals from PES read-head 525 when PES read-head 525 reads servo-alignment marks 526 in servo track 527. Based on this PES information, processor 524 sends a signal to power amplifier 528 to control X-axis actuator 529 which in turn controls the motion of head module 520 in the X-axis direction. With X-axis actuator 529 connected to head-module 520 via mechanical connector 530, head-module 520 may be positioned to center write-head 522 and read-sensor 523 on biosample track 521. Processor 524 may send signals to power amplifier 531 to control Y-axis actuator 532 for conducting a scan by head module 520 across substrate 533. With Y-axis actuator 532 connected to X-axis actuator 529 via mechanical connector 534, head-module 520 can be moved along the Y-axis in a controllable manner.

As an example, when a predetermined number of servo-alignment marks 526 are read by PES read-head 525, processor 524 stops the Y-axis motion of head-module 520. A servo-system for control of X-axis actuator 529 and head-module 520 along the X-axis direction, particular to servo-alignment marks 526 shown in servo track 527, is taught without limitation by U.S. Pat. No. 5,689,384, entitled "Timing Based Servo System for Magnetic Tape System," which is hereby incorporated by reference in its entirety. The servo-system may comprise other structures with similar functionality. As previously described regarding Z-pattern 210, the velocity of head module 520 relative to substrate 533 along the Y-axis can be calculated by dividing distance AB+BC by the time it takes for head module 520 to transit Z-pattern 210. This velocity measurement can be used by processor 524 to control Y-axis actuator 532 to keep head module 520 at a constant Y-axis velocity Vy relative to substrate 533. The position along the Y-axis of head module 520 relative to substrate 533 can be obtained by counting servo-alignment marks 526 or Z-pattern 210 by PES read head 525 and processor 524.

FIG. 6 shows an exemplary embodiment of a write and read circuitry 600 for writing to a biosample track 621 (i.e., for magnetically exciting molecules 402) and reading from the biosample track 621 (i.e., for sensing and identifying the magnetically excited molecules 402) on substrate 633. Processor 624 may send signals to power amplifier 646 which provides power to write-head 647 on head module 620 for magnetically exciting molecules 402 with spike (impulse), swept sine, or random noise wave-forms. Processor 624 may further send signals to power amplifier 645 which powers Wheatstone bridge 640. Read-sensor 623 is one component in Wheatstone bridge 640 and thus receives DC current from the Wheatstone bridge 640. Wheatstone bridge 640 serves the function of balancing out the zero-magnetism resistance of read-sensor 623 so that only the change in resistance of read-sensor 623 is passed onto amplifier 641. Such resistance change is due to the detection of a resonating 402, which is sent to amplifier 641 and filter 642 before being received by processor 624.

Filter 642 filters out 60 Hz noise, which is pervasive noise in an office or laboratory with lighting where processes of the invention are typically performed. Processor 624 makes the determination of whether a molecule 402 was detected. The change in resistance of read-sensor 623 is directly proportional to the magnetic field provided by a magnetically excited molecule 402. As a result, processor 624 could register the detection of different molecules 402 during the sensing of read-sensor 623, depending on different frequencies received by the read-sensor 623. The identification of the various molecules 402 simultaneously on the same biosample track 621 may be facilitated by a lookup table 644 in processor 624, as described in detail with reference to FIG. 7. In one exemplary embodiment of the invention, the lookup table 644 contains a list of different molecules 402, and their respective resonance frequencies.

The resonant response table 644 may include a list of known molecules and radicals such as H+, OH—, C—H, H—C—H and the like, and their resonant frequencies, as well as normalized amplitudes of those resonant frequencies. The resonant response table 644 may further include harmonics of the resonant frequencies, if they exist. The resonant frequencies, normalized amplitudes, and harmonic frequencies assist in the identification of the chemical composition of the magnetically excited molecules. A matched filter 643 may be present to provide a correlation between ideal resonances and the measured resonances, and resonances are considered to be detected if the correlation exceeds a user-selectable threshold, such as 80%, where 0% indicates no correlation and 100% indicates a perfect correlation. PES read head 625, alignment servo marks 626, and servo track 627 are identical to 525, 526, and 527 of FIG. 5, respectively.

Figure 7:
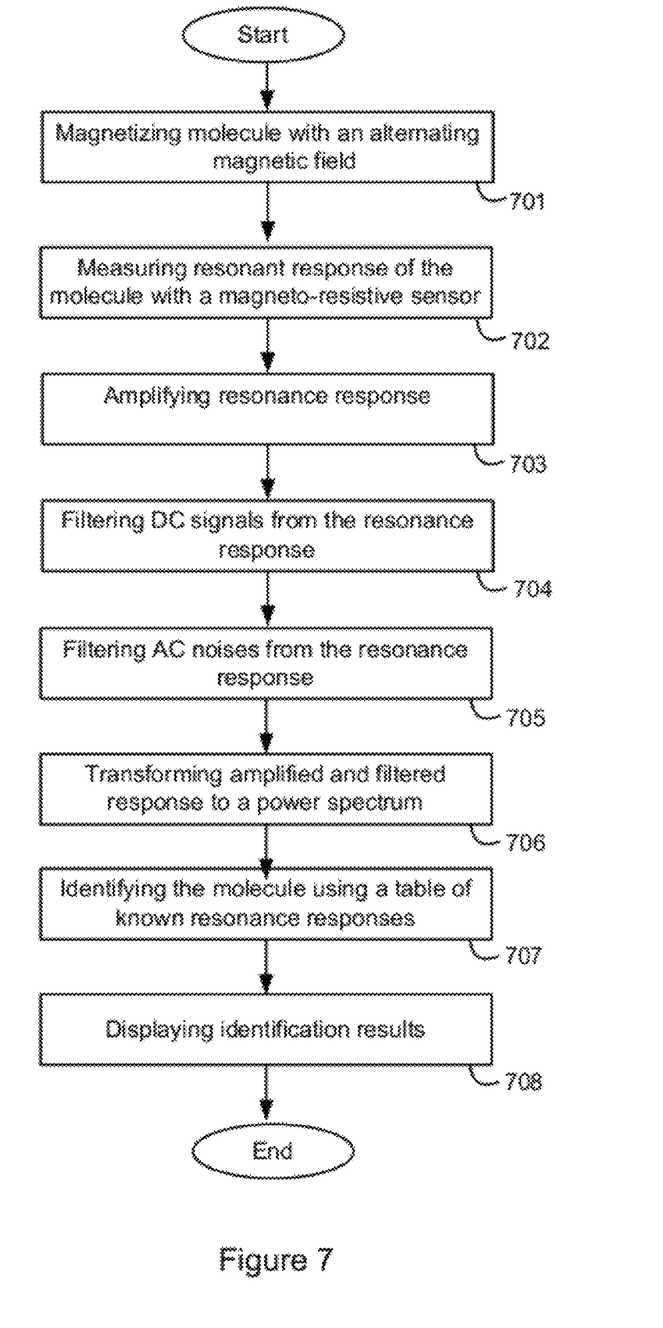
FIG. 7 is a flowchart illustrating an exemplary process for identifying a molecule using an electromagnetic read-write head, in accordance with an embodiment of the invention.

FIG. 7 is a flowchart illustrating an exemplary process for identifying a molecule using an electromagnetic read-write head, in accordance with an embodiment of the invention. The process may be performed by an excitation-response molecular-identification system, such as system 400, on a biosample as illustrated in FIGS. 1-3. Such an analytical system 400 may include appropriate electrical circuits, devices, computer hardware and program instructions to carry out the illustrated operations. At step 701, an electromagnetic write-head 403 receives an alternating AC current and generates an alternating magnetic field which magnetically excites a target molecule 402. This magnetization causes an oscillation of the atoms in the molecule 402.

In one embodiment, the alternating magnetic field generated by write-head 403 is supplemented by a steady-state, non-oscillating magnetic field, which may be supplied by a permanent magnet or an electromagnet supplied with direct DC current. Such a non-oscillating magnetic field tends to align the atoms in the molecule to maximize the excitation provided by the alternating magnetic field, thus increasing the signal-to-noise ratio (SNR). In an alternate embodiment, the write-head 403 generates the non-oscillating magnetic field that is superimposed over the alternating magnetic field.

In one embodiment, the excitation provided by the power supply feeding write-head 403, and hence the alternating magnetic field generated by write-head 403 may be a swept-sine signal. The swept-sine signal is a simple sine wave with a frequency that changes over time and may be generated by a signal generator 415. Generally the frequency of the sine wave starts at a low frequency and increases with time. Alternatively, the frequency of the sine wave starts at a high frequency and decreases with time.

In another embodiment, the alternating magnetic field generated by write-head 403 may be a white noise excitation, which is the statistical equivalent of random noise. An example of white noise is the static one hears on an AM radio. The random noise signal may be generated by sending a reverse polarity voltage across a diode.

In a yet another embodiment, the alternating magnetic field generated by write-head 403 may be an impulse signal, which is a narrow square wave of a single magnetic polarity. The square wave is applied only once by the write-head 403 during a sample period, i.e., during the measurement of the resulting resonant response from the excited molecule 402. The read-sensor 108 may register the resonant response only after the generation of the impulse "spike" wave is completed by write-head 403.

The goal of the swept sine, white noise, and impulse excitations is to cause the molecule 402 to resonate, and it is this resonance which is detected by read-sensor 404. This resonance may comprise one or more fundamental resonances, and each fundamental resonance may have harmonic resonances which are integer multiples of the fundamental resonance. For example, a fundamental resonance of frequency $\omega 1$ may have a first harmonic of frequency $2*\omega 1$, a second harmonic of frequency $3*\omega 1$, a third harmonic of frequency $4*\omega 1$, etc.

When the atoms in a molecule 402 are magnetically excited, the molecule 402 generates a resonant response that may be detected and measured by a magneto-resistive read-sensor 404 in step 702. The magneto-resistive read-sensor 404 may be, for example, a GMR sensor, a TMR sensor, or an AMR sensor. The use of these sensors, which are generally used in data storage tape systems, provides an advantage when using the tape systems to detect and analyze antigens. In order to facilitate the measurement of the resonant response from the magnetically excited molecule 402, the analytical system 400 may expose the molecule 402 to a DC magnetic field while the molecule 402 is being magnetically excited by the alternating magnetic field.

Magnetic shield 305, as illustrated in FIG. 3, separates write-head 403 and read-sensor 404 so that there is no harmful cross-talk between write-head 403 and read-sensor 404 during steps 701 (molecule excitation) and 702 (resonant response measurement). Read-sensor 404 is typically one leg of a Wheatstone bridge, so that the nominal (zero-excitation) resistance of the read-sensor 404 may be zeroed-out by balancing the Wheatstone bridge. Accordingly, the output of the Wheatstone bridge is only the change in resistance experienced by the read-sensor 404 as it detects the resonances of the target molecule 402.

The resonant response from the magnetically excited molecule 402 that the magneto-resistive read-sensor 404 measures is generally too small for positively identifying the molecule 402. Thus, an amplifier 641 in the detection circuit 600 may be employed to amplify the measured response at step 703. Amplifier 641 is typically a solid state amplifier with predetermined gains of 10×, 100× and 1000×. Such solid state amplifiers may allow user controlled gain. In addition, the measured resonant response from the magnetically excited molecule 402 may include a zero-magnetism resistance of read-sensor 623. This DC signal may be filtered out from the resonant response, at step 704, by balancing a resistive Wheatstone bridge in which one leg of the Wheatstone bridge is the magneto-resistive sensor 404. Such a Wheatstone bridge is illustrated in FIG. 6. The DC signal filtering assures that only changes in resistance of read-sensor 623 are passed to the amplifier 641.

At step 705, a filter 642 in the detection circuit 600 may be employed to eliminate AC background noise, such as 60 Hertz noise emanated by common lighting and electric power equipment in a laboratory. As examples, the noise filter 642 may be a band pass filter, band block filter, high-pass filter, Hamming filter, or Butterworth filter, which are known to one skilled in the art.

The amplified and filtered resonant response of the magnetically excited molecule 402 may be further transformed to a power spectrum at step 706 to facilitate the identification of fundamental frequencies and harmonic frequencies, as follows. First, a Fourier transform $F(\omega)$ is created of the filtered and amplified output $\omega$ of the Wheatstone bridge, of which read-sensor 404 is a part. Fourier transform $F(\omega)$ is in the frequency domain, and is the frequency representation of the time-domain signal from read-sensor 404. Next, the Fourier transform $F(\omega)$ is multiplied by its complex conjugate $F^*(\omega)$ to give the power spectrum $\Phi(\omega)$ per equations (1) and (2). Equation (1) is for an analog Fourier transform, one which is continuous in frequency. Equation (2) is for a digital Fourier transform, which is expressed, for example, in discrete increments in frequency.

$$\Phi(\omega) = \left| \frac{1}{\sqrt{2\pi}} \int_{-\infty}^{\infty} f(t) e^{-i\omega t} dt \right|^2 = \frac{F(\omega) F^*(\omega)}{2\pi} \quad \text{Equation (1)}$$

$$\Phi(\omega) = \left| \frac{1}{\sqrt{2\pi}} \sum_{n=-\infty}^{\infty} f_n e^{-i\omega n} \right|^2 = \frac{F(\omega) F^*(\omega)}{2\pi} \quad \text{Equation (2)}$$

The resonances and harmonic frequencies are peaks in the power spectrum $\Phi(\omega)$ and may be identified by peak-detect algorithms, as known in the art, such as used in recording technology such as for tape drives. The resonances and harmonic frequencies detected by the read-sensor are compared to a table of known resonant responses for known chemical radicals, such as H+, OH—, C—H, H—C—H, etc. From this table, and the aforementioned resonances and harmonic frequencies, the chemical composition the target molecule 402 is identified, at step 707. Once the molecule 402 is identified, the analytical system 400 may present the results of the molecule scan to a physician or clinician at step 708, for example, by informing the physician or clinician of the presence or absence of target molecules in the biological sample.

Referring again to FIG. 1, there may be multiple target molecules in the biosample tracks 180 that the excitation-response process described above may identify. If there are more biosample tracks 180 than write-head 106 and read-sensor 108 pairs in head-module 104, head-module 104 may scan the biosample tracks 180 in a serpentine pattern. The head-module 104 performs a scan in the +Y direction, as head-module 104 only provides read-after-write capability in the +Y direction as illustrated in FIG. 1. Then a second head-module comprising a mirror image of head-module 104 may perform a read-after-write operation in the -Y direction. In one embodiment, during the excitation-response process, the write-head 106 and read-sensor 108 pairs are stationary and physical motion along the +/-Y direction only occurs in moving from one sample site to the next. The use of IBM's Timing Based Servo, as read by a servo read-head on head module 104, may assist in the guiding of write-head 106 and read-sensor 108 from one target molecule to the next.

To facilitate the detection of different target molecules, calibration of read-sensor 108 may be performed. An exemplary read-sensor calibration process is described, for example, in the commonly-assigned patent application entitled "A Circuit For Detecting Analytes Via Nanoparticle-labeled Substances With Electromagnetic Read-Write Heads", Ser. No. 12/888,408, herein incorporated by reference in its entirety. The calibration process may use of a variety of known molecules positioned in known locations in biosample tracks 180, where the resonant responses of these molecules are known. Variants of known molecules are formed of atoms of carbon isotopes. For example, Carbon-12 is replaced by Carbon-13 or Carbon-14. This affects the resonances of the known molecule, causing a shift in the resonant frequencies, because of the change of mass of the atoms. magnetically excited nanoparticles of known magnetic intensity may be used in fixed positions along biosample track 180 to "label" the known molecules used for calibration purposes. These nanoparticle labels would typically be of a high coercivity, such as Barium Ferrite, so that the magnetization of these nanoparticles is not affected by write-head 106 during the excitation-response molecular-identification process.

While the exemplary embodiments of the invention have been illustrated and described in detail, it should be apparent that modifications and adaptations to those embodiments may occur to one skilled in the art without departing from the scope of the invention. Aspects of the present disclosure may be embodied as a method, system or computer program product, and may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a wide area network (WAN), Ethernet, or the connection may be made to an external computer, for example, through the Internet using an Internet Service Provider.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures described above illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. An apparatus for identifying a molecule, comprising:
   a biosample substrate comprising a magnetic tape medium having a plurality of biosample tracks, configured to attach thereto a molecule to be identified;
   an electromagnetic write-head configured to magnetically excite the molecule to be identified with an alternating magnetic field;
   a magneto-resistive sensor for measuring a resonant response of the magnetically excited molecule to be identified; and
   a processor coupled to the magneto-resistive sensor for comparing the resonant response to a table of known resonant responses to identify a chemical composition of the molecule to be identified.

2. The apparatus of claim 1, further comprising a magnet configured to expose the molecule to be identified to a DC magnetic field while the molecule to be identified is being magnetically excited by the alternating magnetic field to facilitate the measurement of the resonant response.

3. The apparatus of claim 2, wherein the magnet is a permanent magnet or an electromagnet.

4. The apparatus of claim 1, wherein the magneto-resistive sensor is selected from the group consisting of a GMR sensor, a TMR sensor, and an AMR sensor.

5. The apparatus of claim 1, wherein the plurality of biosample tracks are further configured to attach thereto a molecule to be identified encapsulated in a carbon nanotube to keep the molecule in position during the magnetic excitation.

6. The apparatus of claim 1, wherein the alternating magnetic field is characterized by a random-noise signal.

7. The apparatus of claim 6, wherein the random noise signal is generated by sending a reverse polarity voltage across a diode.

8. The apparatus of claim 1, wherein the alternating magnetic field is characterized by an impulse signal having a generally narrow square-wave spike, and the generally narrow square-wave spike is applied once during the measurement of the resonant response.

9. The apparatus of claim 1, further comprising a Wheatstone bridge coupled to the magneto-resistive sensor, the Wheatstone bridge being configured to filter out a DC signal from the resonant response.

10. The apparatus of claim 1, further comprising a filter coupled to the magneto-resistive sensor and configured to filter out AC noise signals from the resonant response, said filter selected from the group consisting of a band pass filter, a band block filter, a high-pass filter, a Hamming filter, and a Butterworth filter.

11. The apparatus of claim 1, further comprising an amplifier coupled to the magneto-resistive sensor and configured to amplify the resonant response.

12. The apparatus as recited in claim 1, wherein the electromagnetic write-head and the magneto-resistive sensor are components of a single device within the apparatus, and
   wherein the single device performs both of the magnetically exciting the molecule to be identified and the measuring the resonant response of the magnetically excited molecule to be identified.

13. The apparatus as recited in claim 1, wherein the alternating magnetic field is characterized by a swept sine function, and
   wherein the electromagnetic write-head is further configured to generate the alternating magnetic field characterized by the swept sine function.

14. The apparatus as recited in claim 1, further comprising:
a plurality of the electromagnetic write-heads; and
a plurality of the magneto-resistive sensors,
   wherein the electromagnetic write-heads and the magneto-resistive sensors are arranged in a plurality of head/sensor pairs, each head/sensor pair being configured to:
      magnetically excite a molecule to be identified, each molecule to be identified being disposed in one of the plurality of biosample tracks of the biosample substrate; and
      measure the resonant response of each magnetically excited molecule to be identified, and
   wherein the apparatus is further configured to align each head/sensor pair with one of the plurality of biosample tracks in the biosample substrate.

15. The apparatus as recited in claim 14, wherein the biosample substrate further comprises a Peltier substrate.

16. The apparatus as recited in claim 14, wherein the plurality of head/sensor pairs includes at least eight head/sensor pairs.

17. The apparatus as recited in claim 14, wherein the alternating magnetic field is characterized by a swept sine function, and
   wherein each head/sensor pair is further configured generate the alternating magnetic field characterized by the swept sine function.

18. A method of identifying a molecule, comprising:
positioning an electromagnetic write-head in proximity to a biosample substrate, the biosample substrate comprising a magnetic tape medium having a plurality of biosample tracks, and at least one of the biosample tracks having disposed thereon a molecule to be identified;
magnetically exciting the molecule to be identified with an alternating magnetic field generated by the electromagnetic write-head;
measuring a resonant response of the molecule to be identified with a magneto-resistive sensor; and
comparing the resonant response to a table of known resonant responses to identify a chemical composition of the molecule to be identified.

19. A computer program product comprising a computer readable storage medium having computer readable program code embodied therewith, the computer readable program code comprising:
   program code configured to position an electromagnetic write head in proximity to a biosample substrate, the biosample substrate comprising a magnetic tape medium having a plurality of biosample tracks, and at least one of the biosample tracks having disposed thereon a molecule to be identified,
   program code configured to magnetically excite the molecule to be identified with an alternating magnetic field generated by the electromagnetic write-head;
   program code configured to measure a resonant response of the molecule to be identified with a magneto-resistive sensor; and
   program code configured to compare, at least partially using the processor recited in claim 1, the resonant response to a table of known resonant responses to identify a chemical composition of the molecule to be identified.

* * * * *